(12) United States Patent
Edelman et al.

(10) Patent No.: US 7,176,352 B1
(45) Date of Patent: Feb. 13, 2007

(54) TRANSGENIC LEMNACEAE

(75) Inventors: Meir Edelman, Rehovot (IL); Avihai Perl, Rishon LeZion (IL); Moshe Flaishman, Ramat Aviv (IL); Amnon Blumenthal, Rehovot (IL)

(73) Assignee: Yeda Research and Development Company Ltd., Rehovot (IL)

( * ) Notice: Subject to any disclaimer, the term of this patent is extended or adjusted under 35 U.S.C. 154(b) by 560 days.

(21) Appl. No.: 09/529,172

(22) PCT Filed: Oct. 8, 1998

(86) PCT No.: PCT/IL98/00487

§ 371 (c)(1), (2), (4) Date: Aug. 22, 2000

(87) PCT Pub. No.: WO99/19498

PCT Pub. Date: Apr. 22, 1999

Related U.S. Application Data

(63) Continuation-in-part of application No. PCT/IL97/00328, filed on Oct. 10, 1997.

(51) Int. Cl.
*C12N 15/82* (2006.01)
*A01H 1/00* (2006.01)
*C12N 5/14* (2006.01)

(52) U.S. Cl. .................................... 800/294

(58) Field of Classification Search ............... 435/468, 435/469, 496, 69.1; 800/278, 294, 295, 298
See application file for complete search history.

(56) References Cited

U.S. PATENT DOCUMENTS 6,040,498 A * 3/2000 Stomp et al. ............... 800/294

FOREIGN PATENT DOCUMENTS

| DE | 196 29 402 | 2/1998 |
| EP | 0 249 432 | 12/1987 |
| GB | 2 211 204 | 6/1989 |
| WO | 87 07299 | 12/1987 |
| WO | 89 12102 | 12/1989 |
| WO | 95 15678 | 6/1995 |
| WO | WO 99/07210 A1 | 2/1999 |

OTHER PUBLICATIONS

Stachel et al., Nature, 1985, vol. 318, pp. 624-629.*
Welch et al., Mol. Cell. Biol., 1985, vol. 5, pp. 1229-1237.*
Bechtold et al., C.R. Acad. Sci., Paris, Sciences de la vie/Life Sciences, 1993, vol. 316, pp. 1194-1199.*
Grimsly, N., Agroinfection, In Methods in Molecular Biology, vol. 44: Agrobacterium Protocols, 1995, K.M.A. Gartland and M.R. Davey, Eds, Humana Press Inc., Totowa, N.J.*
Moon et al., "Effects of Medium Components and Light on Callus Induction, growth, and Frond Regeneration in *Lemna gibba* (DUCKWEED)", *In Vitro Cellular and Development Biology-Plant*, (1997), vol. 33, pp. 20-25.
Chang et al., "Regeneration of *Lemna gibba* G 3 through Callus Culture", *Z. Pflanzenphysiol. Bd.*, (1978), vol. 89, pp. 91-94, China.
Chang et al., "Callus Formation and Regeneration of Frond-Like Structures in *Lemna perpusilla*, 6746 on Defined Medium", *Plant Science Letters*, (1978), vol. 13, pp. 133-136.
Tobin et al., "Phytochrome Regulation of Transcription: Biochemical and Genetic Appraches", *NATO ASI Series*, (1991), vol. H50, pp. 167-179.
Frey et al., "Evidence for Uptake of Plamid DNA into Intact Plants (*Lemna perpusilla*) proved by an *E. coli* Transformation Assay", *Zeitschrift Fur Naturforschung*, (1980), vol. 35c, pp. 1104-1106.
Vernade et al., "Glycine Betaine Allows Enhanced Induction of the *Agrobacterium tumefaciens* vir Genes by Acetosyringone at Low pH", *Journal of Bacteriology*, (1988), vol. 170, No. 12, pp. 5822-5829.
Chemical Abstracts, Lin et al., "Effects of gamma-rays and caffeine on young inflorescence cultures of wheat", vol. 5, No. 3.
Dudley et al., "Production, Chemical Quality and use of Duckweeds (Lemnaceae) in Aquaculture, waste Management, and Animal Feeds", *J. World Maricul. Soc.*, (1981) vol. 12, No. 2, pp. 27-49.
Porath et al., "Duckweed as an Aquatic Crop: Evaluation of Clones for Aquaculture", *Aquatic Botany*, (1979), vol. 7, pp. 273-278, The Netherlands.
Landolt, "The Family of (Lemnaceae)- a monographic study" *Biosystematic Investigations in the Family of Duckweeds (Lemnaceae)* (1986), vol. 1, pp. 272-274.
Yukoh Hiel et al., "Efficient Transformation of Rice (*Oryza sativa* L.) Mediated by *Agrobacterium* and Squence Analysis of the Boundaries of the T-DNA", *The Plant Journal*, 1994, pp. 271-281, vol. 6, No. 2.
Sung Hun Park et al., "T-DNA Integration into Genomic DNA of Rice Following *Agrobacterium* Inoculation of Isolated Shoot Apices", *Plant Molecular Biology*, 1996, pp. 1135-1148, vol. 32.
Willi Schäfer et al., "T-DNA Integration and Expression in a Monocot Crop Plant After Induction of *Agrobacterium*", *Nature*, Jun. 11, 1987, pp. 529-531, vol. 327.

* cited by examiner

*Primary Examiner*—Ashwin Mehta
(74) *Attorney, Agent, or Firm*—Browdy and Neimark, PLLC

(57) ABSTRACT

The present invention concerns genetically stable transformed *Lemnaceae* plants and methods for their transformation by *Agrobacterium* cells. The present invention further concerns a method for regeneration of plants from calli, utilizing low sucrose media and products of interest produce from said plants. The present invention further concerns booster media for use in the above methods.

26 Claims, 1 Drawing Sheet

TRANSGENIC LEMNACEAE

CROSS REFERENCE TO RELATED APPLICATION

The present application is the national stage under 35 U.S.C. 371 of PCT/IL98/00487, filed 8 Oct. 1998.

FIELD OF THE INVENTION

The present invention relates to stably transformed plants, progeny thereof and products obtained from the cells or progeny. The invention further concerns methods for the genetic transformation of plants and more specifically to a method wherein *Agrobacterium* is used as the transforming vector.

PRIOR ART

The prior art considered to be pertinent to the following disclosure is listed in the section entitled "References" before the claims.

BACKGROUND OF THE INVENTION

Genetic transformation of plants is gradually beginning to play an important role in modern agriculture. Attempts are made to introduce heterologous DNA into plants in order to increase their resistance to viral infection, acquire or increase resistance to various herbicides, modulate ripening or decay times, increase the nutritional value of various plant products, bring them to produce pharmaceuticals, and produce various other chemical and biological molecules.

Commercial production of transgenic compounds in bacterial, yeast and mammalian cell systems is often beset by high capital investment costs in fermentation equipment and the necessity to eliminate prion or microplasmal components from the purified product. Recently, production of heterologous proteins and peptides (e.g., α-amylase, antibodies, enkephalins, human serum albumin) has been achieved in plants (Pen et al., 1992, Miele, 1997). Potential advantages of transgenic plants systems are: lowered production costs of biomass and a reduction in the biohazard of contaminants in downstream processing of the products. Transgenic plants may thus be superior bioreactors for bulk enzymes in industry, purified products in medicine and orally active pharmaceuticals.

In order to transform plants to produce a desired product, the relevant gene, once identified and cloned, has to be introduced into the plant of interest so that the resulting plant is capable of passing the gene to its progeny. The methods of introduction proposed for this purpose include electroporation, microinjection, microprojectile bombardments, liposome fusion, *Agrobacterium* mediated transfer, and many others.

One of the most commonly used transforming vectors is *Agrobacterium*, which is a genus of plant pathogenic bacteria of the family *Rhizobiaceae*, which does not fix free nitrogen and usually produces gall and hairy roots in infected cells. Heterologous DNA is introduced into the *Agrobacterium* and through a process of transfection wherein genetic material from the *Agrobacterium* enters the plant's cell, genetic transformation of the plant takes place (Armitage et al., 1992). *Agrobacterium* infects primarily dicotyledonous plants and infects monocotyledonous plants only at a very low yield (Armitage et al., 1992).

One attempt to transform monocotyledonous plants was by a particle gun wherein the heterologous DNA is delivered by air or by helium into the plant or plant cell to be transformed. This technique has two main disadvantages: first, it is quite difficult to target the DNA particles to the meristematic zone wherein, for certain plants such as those of the family *Lemnaceae*, the transformation should take place in order to enable regeneration therefrom of a full transformed plant; second, even if the DNA particle enters the cell in the meristematic zone and reaches the nucleus thereof, the DNA does not usually integrate into the cell's chromosome and, thus after a few cell cycles the unintegrated heterologous DNA is lost, so that transformation by a particle gun is usually merely transient.

It would have been highly desirable to provide a method for the genetic transformation of monocotyledonous plants which would result in stable transformation with a satisfactory yield.

One of the most commercially promising monocotyledons are the *Lemnaceae*, a widely distributed aquatic family of small (1–5 mm) plants. The *Lemnaceae* excel in two characteristics potentially exploitable by the biotechnology industry: their extraordinary vegetative growth rates and a high tolerance for a spectrum of nutrients and toxic substances (Landolt and Kandeler, 1987). In the U.S.A., commercialization of *Lemnaceae* has centered around waste water management and animal feed (Culley et al., 1981; Ngo, 1987). However, the use of mixed aquacultures and conventional technology has met with only moderate success. A different approach was taken in Israel, utilizing the *Lemna gibba* Hurfeish strain (Porath et al., 1979). With its especially short root and high protein, carotenoid and iron content, this strain was cultivated under modern greenhouse conditions (4 tons harvested per acre per week; Tzora Biotechnology Inc., Kibbutz Tzora), and successfully marketed as a packaged vegetable product for the food industry. Notwithstanding the exceedingly high growth rates and the promising future of *Lemnaceae* as a potential food source, various attempts to genetically transform these plants, by a stable transformation method proved, to date, quite unsuccessful. The failure of transformation was due to the fact that *Lemnaceae* multiply vegetatively, daughter fronds arising from meristematic zones deep inside the mother frond. Thus, the meristem initial must be reached for stable transformation to take hold. Particle bombardment of *Lemnaceae*, the current state-of-the-art method used by several groups to obtain localized, transitory transformation events, was found by the inventors of the application ineffective in transformation of daughter fronds.

It would have been highly desirable to obtain *Lemnaceae* plants which are stably transformed with heterologous DNA of interest and to use such transformed plants for the production of chemical and biological products.

GENERAL DESCRIPTION OF THE INVENTION

In the following description, the term "transformation" will be used to denote the introduction of a transforming DNA into plant cells or tissues which brings to the appearance in these cells or tissues of traits which said cells or tissues did not possess beforehand or to modulation of traits present, a priori, in the plants. The term "stable transformation" will be used to denote such a genetic transformation which is heritable to future generations of the transformed plant. The term "transforming DNA" will be used herein to denote a foreign DNA molecule which is introduced into plant cells and causes their transformation. The transforming DNA may be of any origin, for example plant origin, and may also be a DNA sequence which is naturally present in the transformed plant. The transforming DNA may comprise coding sequences and/or control sequences capable of regulating the amount and time of the transcription. The term "stably transformed plant" will be used hereinafter to denote a plant comprising a transforming DNA stably integrated in its genome. A "stably transformed *Lemnaceae*" conforms to the description of a stably transformed plant.

In accordance with the present invention it was surprisingly found that there exist conditions which allow stable transformation of *Lemnaceae* plants. Thus, by one of its aspects, the present invention concerns a stably transformed *Lemnaceae* plant, tissues, products thereof and progeny thereof.

The *Lemnaceae* plants are preferably of the genera: *Spirodela*, *Lemna* and *Wolffia*. The present invention preferably concerns transformed *Lemnaceae* strains capable of exceptionally high efficiency of transformation, an example of such a strain being *Spirodela punctata* strain 8717, which is a *Spirodela punctata* strain isolated by E. Landolt and erroneously labeled as *Lemna disperma* in Landolt 1986.

The transformed *Lemnaceae* plant, tissue and products thereof of the invention may be used for the production of various chemical and biological products such as proteins and polypeptides encoded by the transforming DNA and may also be used to prepare various enzymes capable of producing various chemicals such as carbohydrates, lipids, alkaloids, pigments, vitamins, etc.

The present invention also concerns a method of production of a product of interest, for example chemical and biological products such as proteins, polypeptides, carbohydrates, lipids, alkaloids, pigments, vitamins, and others, wherein a transformed *Lemnaceae* according to the invention is grown in an appropriate culture medium, to produce the product of interest. The product of interest may be further isolated and purified, totally or partially, for a further use, in order to serve as a food additive, a cosmetic additive, a vaccine, therapeutic agent, a biocatalyst for enzymatic conversion of chemicals, etc. Alternatively, the product of interest may be used in its raw, unisolated form as present in the grown *Lemnaceae* plant, by using the plant with no or partial processing itself for the above purposes.

The present invention is also concerned, by another of its aspects, with a product of interest being a chemical or biological product such as proteins, polypeptides, carbohydrates, lipids, alkaloids, pigments, vitamins, and others, obtained from the above stably transformed *Lemnaceae* plants.

The transformed plant or tissue may also express desired traits which are not featured in production of new products, examples of such traits are: antibiotic resistance, for example, kanamycin resistance, conferred by the npt II gene; or herbicide resistance, for example, resistance to the herbicited BASTA 20 (ammonium, glufosinate, Hoechst, Germany)

The transferred *Lemnaceae* plants or tissue may also express more than one foreign gene, for example, the plant may be transformed to be resistant to several herbicides and/or antibiotics at once.

In accordance with the present invention, it was found that stable transformation of *Lemnaceae* plants or tissue may be obtained by the use of *Agrobacterium* cells carrying said transforming DNA. Thus, in accordance with a further of its aspects, the present invention concerns a method for the stable transformation of *Lemnaceae* plants or tissue which comprises incubating *Lemnaceae* plants or plant tissue with *Agrobacterium* cells carrying said transforming DNA, whereby cells in said plant tissue become stably transformed by said transforming DNA.

It was further found that there exists *Agrobacterium* strains which can specifically target and transform meristematic tissue in *Lemnaceae*, for example *A. tumefaciens* strains EHA105, EHA101 and GVE3103, or *Agrobacterium* strains which can specifically target and transform the wounded area of the plant such as *A. tumefaciens* strains LBA4404 and C58. Therefore the method of the invention preferably concerns incubation of *Lemnaceae* plants with *Agrobacterium* of the strains. EHA105, EHA101 and GVE3103 capable of transforming the meristematic tissue or *Agrobacterium* strains LBA4404 and C58 capable of transforming wounded tissue.

It was still further found that use of vacuum filtration during the incubation of the *Lemnaceae* plants with the *Agrobacterium* cells increases the efficiency of transformation. Thus, by a preferred embodiment, the method of transformation includes incubation of *Lemnaceae* plants or tissue with *Agrobacterium* cells while applying vacuum infiltration.

Another embodiment of the method of the invention is based on the finding that it was possible to increase the efficiency of *Lemnaceae* transformation by *Agrobacterium* by exposing the meristematic zone of the mother frond. Such exposure can be carried out physically, i.e., by removing the daughter frond to expose the meristematic zone, for example, by a plucking motion using forceps, or by any other mechanical means. Alternatively, said exposure may be carried out by applying chemical preparation or a hormone preparation capable of specifically removing the daughter found without damaging the underlying meristematic zone.

Yet another aspect of the present invention concerns a novel method for plant transformation using transforming *Agrobacterium* cells, which is particularly suitable for mass transformation of plant tissue. In accordance with this method, plants are cut into small particles which are then incubated with the transforming *Agrobacterium* cells, preferably in the presence of the booster medium which will be described hereinbelow. The size of the particles should be such that at least some of them will contain undamaged meristematic tissue which is capable of regenerating into full plants. In order to achieve this feature, the particles should preferably be at an average size of above 150 µm in diameter, most preferably at a size range of about 150 µm–750 µm. Cutting the plant tissue into such small particles maximizes the contact area between the meristematic tissue and the *Agrobacterium*. Furthermore, *Agrobacterium* cells more readily infect damaged plant tissue and by cutting the plant, the *Agrobacterium* cells are exposed to large regions of damaged plant tissue. The overall result of these factors is a marked increase in the transformation yield.

Another transformation method which may be used in the performance of the present invention, is microinjection which is known per se. In accordance with this method, *Agrobacterium* cells, preferably together with the booster medium of the invention which will be described hereinbelow, are microinjected to a desired zone of transformation within the plant, typically into the plant's meristem. One major advantage of microinjection, is that it allows specific targeting of the transforming *Agrobacterium* cells to a desired tissue, e.g., only to the roots' meristem, only to the leaves' meristem, etc., so that the result is a plant having foreign DNA only at a specific tissue, for example, the roots and not in other tissues.

Another embodiment of the method of transformation of *Lemnaceae* is based on the surprising finding that transformation can be carried out in planta, i.e. utilizing the full plant and there is no need to cut the plant to small particles, or to use tissue culture and then in vitro regeneration for transformation purposes. A full plant can be used for transformation provided that the *Agrobacterium* cells are targeted to the meristem either by direct microinjection as described above or by utilization of *Agrobacterium* strains which preferably target the meristem such as *A. tumefaciens* strain EHA105, EHA101 and GVE3103. Thus the present invention provides a method for in planta transformation of *Lemnaceae* by targeting *Agrobacterium* cells carrying the transforming DNA to the meristem of the plant to be transformed.

In accordance with another embodiment of the invention, it was found that it is possible to increase the efficiency of transformation of plants by *Agrobacterium* cells by incubating the *Agrobacterium* cells with the plant tissue to be transformed in the presence of a booster medium which is capable of increasing the *Agrobacterium*'s virulence. This increase in efficiency due to use of the booster is not limited to the transformation of *Lemnaceae* plants but it is also applicable to plants in general including monocotyledonous plants and dicotyledonous plants.

*Agrobacterium* is already routinely used for transformation of dicotyledonous plants. However, in accordance with this embodiment of the invention, the efficiency of transformation of dicotyledonous plants is increased by incubation of the *Agrobacterium* booster medium. With respect to monocotyledonous plants, although there have been some reports of a few successful transformations of such plants by *Agrobacterium*, these reports have been sporadic and usually showed unsatisfactory transformation yields. Increasing *Agrobacterium*'s virulence by the booster medium, in accordance with said embodiment, allows for the first time, the transformation of many species of monocotyledonous plants which were previously untransformed, including those belonging to the genus *Lemnaceae*, as well as an increase in the yield of transformation of plants already known to be transformed, albeit at a low yield by the use of *Agrobacterium*.

Stably transformed plants produced by utilizing the booster medium as described above, also form an aspect of the invention.

The booster medium which enhances the virulence of the *Agrobacterium* cells, comprises plant tissue cultured at a pH below about 5.2. For example, the booster medium may comprise a fresh cell suspension of dicotyledonous plants, at a concentration of 1–10% (w/v). The fresh cell suspension may be, for example, from dicotyledonous plants of the *Solanaceae* family.

Preferably, the booster medium also comprises caffeine at a concentration of 100–500 mg per liter of medium.

A specific example of a booster medium is one comprising MS basal medium at a pH of about 3.5–4.2, 1–10% (w/v)) of a fresh cell suspension of *Nicotiana tabacum*, and about 100–500 mg per liter of medium caffeine.

By another alternative, the booster medium of the invention is a plant growth medium comprising *Lemnaceae* plant extracts. Such a medium can be produced by extracting *Lemnaceae* plants in a suitable medium such as phosphate buffer.

Both types of booster mediums, having either or both of the above specifications for use in enhancing transformation efficiency of *Agrobacterium* cells used as a transformation vector, also form another aspect of the invention.

By yet a further embodiment, the present invention concerns a method for maintaining morphogenetic *Lemnaceae* calli for long period of time, by using low levels of sucrose in the growth medium, for example, from 0.1 to 1.5% sucrose. It was found that it is possible to increase significantly the period of maintaining calli in a viable state, for example, from 2 weeks to more than 3 months by decreasing the sucrose level in the growth medium.

Another aspect of the invention concerns a method for the production of highly regenerative *Lemnaceae* calli, and furthermore a method for rapid and efficient regeneration of the plants from the calli, utilizing the combined effect of B5 minerals, low sucrose levels (0.1 to 1.5% sucrose) and phytohormones in the growth medium.

The present invention will now be illustrated with reference to some non-limiting examples.

DETAILED DESCRIPTION OF THE INVENTION

Figure 1:
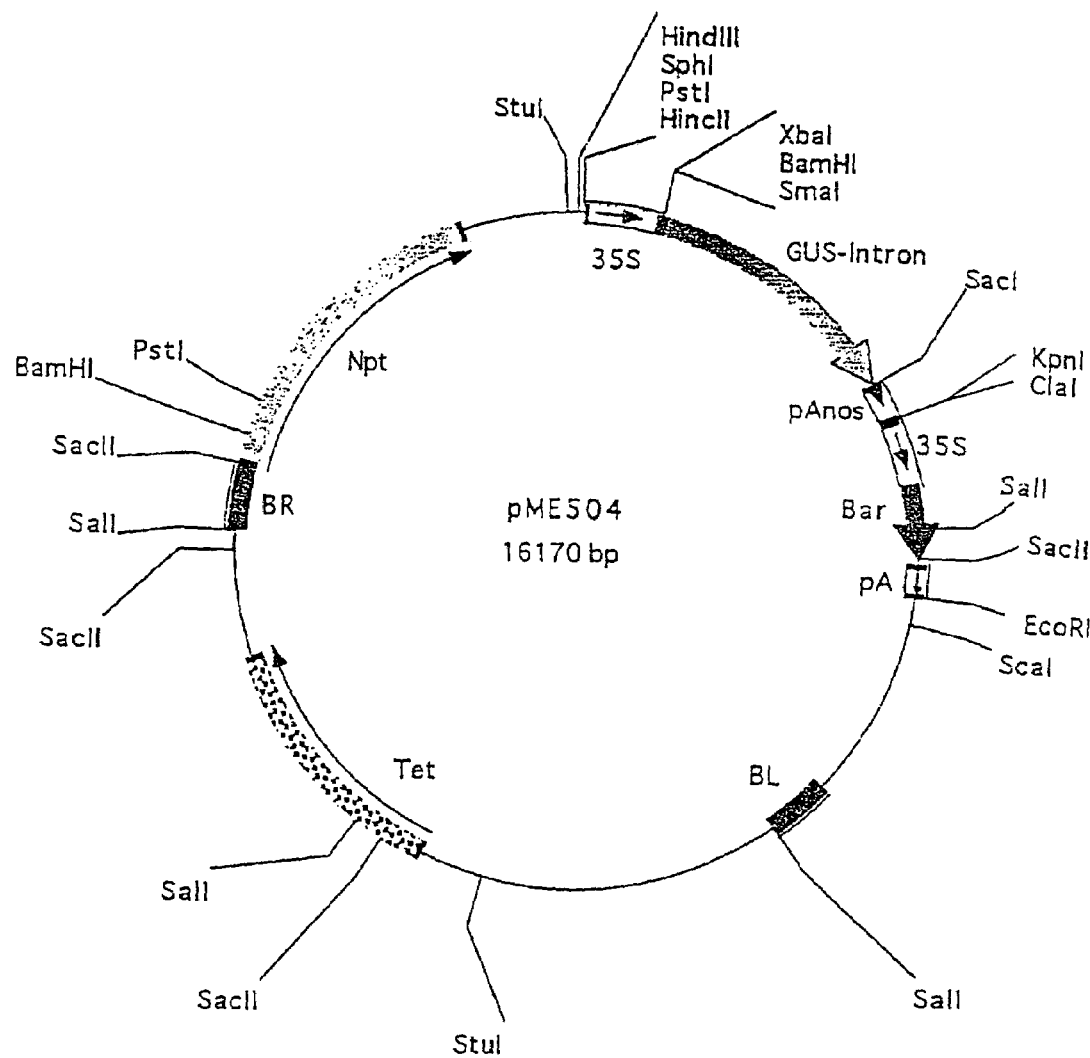
FIG. 1 shows a schematic picture of plasmid Ti pME504.

In the following, the invention will be illustrated at times with specific reference to the transformation of *Lemnaceae* plants, tissue or callus, such reference being given merely as an example and it should be understood that the invention is not limited thereto.

The stably transformed *Lemnaceae* plants contain foreign genes which confer useful traits such as: improvement of nutritional quality of the plant or plant parts; de novo expression of desired chemical and biological products, e.g. enzymes; growth factors, hormones such as insulin; antibodies; anti-oxidants; defensins; proanthocyanidins; cytokines and other biologically active polypeptides and proteins; over-expression of products already expressed by these plants; etc. Other products that may be obtained from the transformed *Lemnaceae* plants are enzymes for industrial applications, such as super-oxide dismutase (SOD), α-amylase, invertase, sucrose phosphate synthase and the like, and chemicals such as food pigments, e.g. β-carotene, anthocyanin, etc. The type of product obtainable from the transformed plants is obviously contingent on the nature of said transforming DNA. By another application the genes may be those which impart disease resistance.

Genes coding for proteins imparting disease resistance are known in the art, including lytic peptides, defensins, oxalate oxydase genes for tolerance to sclerotinia or chitinases (U.S. Pat. No. 5,597,946, U.S. Pat No. 4,940,840, U.S. Pat. No. 5,290,687, U.S. Pat. No. 5,374,540, U.S. Pat. No. 5,670,706, U.S. Pat. No. 5,399,6801, U.S. Pat. No. 5,695,939, all publications incorporated herein by reference).

The transforming DNA which is introduced into the plant cells, include, as will be appreciated by the artisan, coding sequences which code of the desired trait as well as control sequences which control expression of the coding sequence, for example, promotors, enhancers, terminaters, introns and the like, pre-pro peptides or transit peptides, the latter driving the expression of said desired trait in a specific targeted region of the plant cell.

Promoters controlling the expression of genes in plant cells are well known in the field of plant biotechnology, including any promoter sequence of a gene naturally expressed in plants or plant cells, form plant, viral or bacterial origin. Suitable promoters are disclosed in Weising et al. (1988), *Annual Rev. Genet.*, 22: 241), the subject matter of which is incorporated herein by reference. The following is a partial representative list of promoters suitable for use in the context of the invention; regulatory sequences from the T-DNA of *A. tumefaciens*, including mannopine synthase, nopaline synthase and octopine synthase; regulatory sequences from plant origin, including alcohol dehydrogenase promoter from corn, light inducible promoters such as ribulose-biscarboxylase/oxygenase small subunit promoters (SSU RuBisCO) from genes of a variety of species and the major chlorophyl a/b binding gene promoters, histone promoters (EP 507 698), actin promoters (U.S. Pat. No. 5,641,876), maize ubiquitin 1 promoters (Christenses et al., (1996)), regulatory sequences from viral origins, such as 19S or 35S promoters of the cauliflower mosaic virus, (U.S. Pat. No. 5,352,605; U.S. Pat. No. 530,196); developmentally regulated promoters such as waxy, zein, or bronze promoters from maize; as well as synthetic or other natural promoters which are either inducible or constitutive, including those promoters exhibiting organ specific expression or expression at specific development stage(s) of the plant, like the promoter of napin (EP 255 378) or the alpha-tubulin promoter (U.S. Pat. No. 5,635,618); all publications being incorporated herein by reference.

As a preferred embodiment, the promoter is selected among the group consisting in the ribulose-biscarboxylase/oxygenase small subunit promoters (SSU RuBisCO) from genes of a variety of species, the histone promoters, the actin promoters, the maize ubiquitin 1 promoters and the 35S promoters of the cauliflower mosaic virus (CaMV 35S).

According to the present invention, it is possible to use with the promoter, other regulatory elements usually located between the promoter and the coding sequence of the desired trait, which elements induce the expression of the said desired trait in a specific target region of the plant or plant cell, for example, the chloroplasts. Examples of coding sequences for transit peptides, single or combined multiple sequences, the latter may be separated by intermediate sequences. Such multiple transit peptide sequences, such as double transit peptide sequences, may comprise, in the direction of transcription (5' to 3'): a transit peptide of a plant gene encoding a plastid-localized enzyme, a partial sequence of the N-terminal mature part of a plant gene encoding a plastid-localized enzyme and then a second transit peptide of a plant gene encoding a plastid-localized enzyme. An example is the optimized transit peptide disclosed in U.S. Pat. No. 5,510,471 or U.S. Pat. No. 5,633,448 (incorporated herein by reference). The plastid-localized enzymes may be of any origin, for example the small subunit (SSU) of the ribulose, 1,5-diphosphate carboxylase oxygenase (RuBisCO) gene, or the plant EPSPS gene. The signal peptide of the tobacco PR-1a gene described in Cornelissen et al. is another example of a transit peptide.

Another control region may be a terminator or untranslated polyadenylation signal region at the 3' terminus of the coding sequence which may be of any origin, for example bacterial, such as the nopaline synthase gene of *Agrobacterium tumefaciens*, or of plant origin, such as the terminator of the gene coding for the SSU RuBisCO of maize or sunflower, or the terminator of a plant histone gene such as disclosed in EP 633,317, incorporated herein by reference.

Furthermore, the transforming DNA may comprise also a selectable marker gene, such as a gene coding for herbicidal resistance, resistance to antibiotics, or the like. In addition or in the alternative, the transforming DNA may further comprise a reporter gene, such as a gene coding for a color marker. A selectable marker gene or a reporter gene facilitates identification and selection of the transformed tissue and enables its separation from untransformed tissue.

Specific examples of selectable marker genes are the hygromycin phospho-transferase (HPT) coding sequence, which may be derived from *E. coli* and which confers resistance to the antibiotic hygromycin B; the aminoglycoside phospho-transferase gene of transposon Tn5 (AphII) which encodes resistance to the antibiotics kanamycin; neomycin and G418. Genes coding for protein imparting herbicide tolerance are known in the art, including genes imparting tolerance to oxynil herbicides (U.S. Pat. No. 4,810,648 and U.S. Pat. No. 5,559,024), genes imparting tolerance to glyphosate and EPSPS inhibitor herbicides (U.S. Pat. No. 4,535,060, U.S. Pat. No. 4,769,061, U.S. Pat. No. 5,094,945, U.S. Pat. No. 4,940,835, U.S. Pat. No. 5,188,642, U.S. Pat. No. 4,971,908, U.S. Pat. No. 5,145,783, U.S. Pat. No. 5,312,910, U.S. Pat. No. 5,310,667, U.S. Pat. No. 5,633,435, U.S. Pat. No. 5,627,061, U.S. Pat. No. 5,554,798, U.S. Pat. No. 5,633,448, WO 96/04103, all publications incorporated herein by reference), genes imparting tolerance to glufosinate (EP 242 235, incorporated herein by reference), as well as genes imparting tolerance to HPPD inhibitors (WO 96/38567 and WO 98/02562, both publications incorporated herein by reference). Those selectable marker genes which confer resistance or tolerance to these phytotoxic compounds are also of commercial utility in the resulting transformed plants.

Reporter genes may be used for identifying transformed cells, tissue or calli and for evaluating the functionality of regulatory sequences. Reporter genes which code for easily assayable selectable marker proteins are well known in the art. In general, a reporter gene is a gene which is not present in, or expressed by, the recipient organism or tissue and which codes a protein which expression is manifested by some easily detectable property, e.g., phenotypic change or enzymatic activity. Examples of such genes are the chloramphenicol acetyl transferase gene (CAT) from Tn9 of *E. coli*, the β-glucuronidase gene (GUS) of the uidA locus of *E. coli*, the green fluorescence protein (GFP) obtained from *A. Victoria* and the luciferase gene from the firefly *Photinus pyralis*. Expression of the reporter gene is assayed at a suitable time after the DNA has been introduced into the recipient cells. An example of such an assay entails the use of the *E. coli* β-glucuronidase (GUS) gene (Jefferson et al., (1987). Plant cells transformed and expressing this gene will stain blue upon exposure to the substrate, 5-bromo-4-chloro-3-idolyl-β-D-glucuronide (X-GLUC), in the extracellular medium.

According to the method of the invention, *Agrobacterium*, e.g. *Agrobacterium tumefaciens*, is engineered so as to contain the transforming DNA to be inserted into the target plant, e.g. the target *Lemnaceae* plant, which engineering is performed by means known per se. The whole plant or the plant cells tissue or callus are then brought into contact with the *Agrobacterium* cells and incubated together. The plant tissues are then selected for those containing the transforming DNA, for example, by testing for phenotypic expression of the marker gene, e.g. herbicidal or antibiotic resistance, or for the expression of the reporter gene, e.g. a color product. It is also possible to verify the presence of the introduced transforming DNA by a DNA assay such as by PCR.

The invention will now be illustrated further in the following examples:

EXPERIMENTAL PROCEDURES

I. Culture and Maintenance of Lemna and Spirodela for Microinjection Experiments For meristem-zone microinjection, an axenic inoculum (approx. 10 plants) of *Spirodela oligorrhiza* (herein called *Spirodela punctata*) Hegelm, or *Lemna gibba* Hurfeish was introduced in a 250 ml flask containing 50 ml of MS medium having the ingredients as detailed in the following Table 1.

II. Standard Growth Conditions

Cultures were grown at 26° C. under continuous fluorescent light (30 $\mu E$ $m^{-2}s^{-1}$) in a 3–5% $CO_2$-enriched atmosphere.

TABLE 1

Modified MS basal medium (MS medium)
(based on Murashige & Skoog, 1962)

|  | Amount (mg/l) |
|---|---|
| Macro elements | |
| $NH_4NO_3$ | 1650 |
| $KNO_3$ | 1900 |
| $CaCl_2.2H_2O$ | 440 |
| $MgSO_4.7H_2O$ | 370 |
| FeEDTA | 35 |
| $KH_2PO_4$ | 170 |
| Micro elements | |
| $H_3BO_3$ | 6.2 |
| $MnSO_4$ | 22.3 |
| $ZnSO_4.2H_2O$ | 0.25 |
| KI | 0.83 |
| $Na_2MoO_4.2H_2O$ | 0.25 |
| $CuSO_4.5H_2O$ | 0.25 |
| $CoSO_4.7H_2O$ | 0.03 |
| Organic additives | |
| Glycine | 2 |
| Meso-inositol | 100 |
| Thiamine HCl | 10 |
| Nicotinic acid | 0.5 |
| Pyridoxine | 0.5 |
| Biotin | 0.5 |
| Folic acid | 0.5 |
| Casein hydrolysate | 800 |
| Sucrose | 30000 |
| pH brought to 5.8 with NaOH prior to autoclaving | |

III. Standard Transformation Procedure

Under sterile conditions, 2.5 g *Lemnaceae* plants were placed in an empty 9 cm Petri dish. A 10 ml suspension of 5–8×$10^8$/ml *A. tumefaciens*, in MS Basal medium (Table 1) was prepared as described in (IV) below, and added to the dish. Plants were co-cultivated with the *A. tumefaciens* suspension for 20–40 min. at room temperature. The suspension was removed from the dish and the plants washed 3 times with fresh MS Basal medium (Table 1). The plants were transferred to a vessel (15×20×12 cm) containing 1.5 l SP medium (Table 2) at 26° C. under continuous fluorescent light (30 $\mu E$ $m^{-2}s^{-1}$) in a 3–5% $CO_2$-enriched atmosphere.

TABLE 2

SP medium (modified from Hutner) (cf., Posner, 1967)

|  | Amount (mg/l) |
|---|---|
| $KNO_3$ | 300 |
| $Ca(NO_3)_2.4H_2O$ | 72 |
| $MgSO_4.7H_2O$ | 74 |
| $KH_2PO_4$ | 40 |
| NaEDTA | 0.003 |
| Ferric citrate | 1 |
| $H_3BO_3$ | 1 |
| $MnSO_4$ | 0.1 |
| $Na_2MoO_4.2H_2O$ | 0.1 |
| $CuSO_4.5H_2O$ | 0.03 |
| $Z_nSO_4.4H_2O$ | 1 |
| pH brought to 5.8 with NaOH prior to autoclaving | |

IV. Preparation of A. Tumefaciens for Lemnaceae Transformation

A single colony of *Agrobacterium tumefaciens*, maintained on antibiotic-supplemented LB plates (Suppl. LB medium), (Table 3, below), was picked and grown overnight (28° C., 250 rpm) in 10 ml of antibiotic-supplemented 2YT broth (Suppl. 2YT 1 medium;) (Table 4 below). The grown culture was transferred to 50 ml of Suppl. 2YT medium and further grown for an additional 12 hr (28° C., 250 rpm). Before transformation, the *A. tumefaciens* culture was centrifuge (3200×g, 5 min.), the supernatant discarded and the bacteria resuspended in 10 ml of MS medium (Table 1). Before co-cultivation with *Lemnaceae* plants, the bacterial concentration was adjusted to 5–8×$10^8$ cells/ml.

TABLE 3

Supplemented and solidified liquid broth medium
(Suppl. LB medium)

|  | Amount |
|---|---|
| Bacto tryptone | 10 g |
| Bacto yeast extract | 5 g |
| NaCl | 10 g |
| Rifampicin | 25 mg |
| Kanamycin | 50 mg |
| Carbenicillin | 50 mg |
| Cifco agar | 10 g |
| pH brought to 7.0 with NaOH | |

V. Meristem-Zone Microinjection

1. Preparation of Lemnaceae Plants

Axenic *Lemnaceae* plants were cultured in containers (8.5 cm diameter by 11 cm height) containing 50 ml of MS medium (Table 1) at 25° C. under cool white fluorescent bulbs (60 $\mu E$ $m^{-2}s^{-1}$[31]). All treatments were performed in a laminar-flow sterile cabinet at room temperature.

2. Preparation of the Transformation Vector

*Agrobacterium tumefaciens* containing a p35S GUS INT plasmid (Vancanneyt et al. 1990) was utilized. This plasmid carries the NPTII gene coding for kanamycin resistance and the coding sequence of the β-glucuronidase (GUS) uidA reporter gene (Jefferson, 1987) interrupted by the IV2 intron (Eches et al. 1986) Use of this vector enabled staining for GUS expression immediately after transformation and, at the same time, avoided *Agrobacterial*-derived, GUS-positive background. For transformation experiments, a single colony was picked and resuspended in Suppl. 2YT medium, the ingredients of which are detailed in the following Table 4:

TABLE 4

Supplemented 2YT liquid medium (Suppl. 2YT medium)

|  | Amount/liter |
|---|---|
| Bacto tryptone | 16 g |
| Bacto yeast extract | 10 g |
| NaCL | 5 g |
| Rifampicin | 25 mg |
| Kanamycin | 50 mg |
| Carbenicillin | 50 mg |
| pH brought to 7.0 with NaOH | |

The bacteria were cultured for 16 hours on a gyratory shaker (250 rpm) at 28° C. Before co-cultivating the bacterial and the plants, the bacterial culture was diluted with MS medium (Table 1) or booster medium (Table 5, below) to an optical density at 550 mm of 0.6 and brought to pH 4 with HCl. This yielded an *Agrobacterium* preparation suitable for transformation of *Lemnaceae*.

3. Microinjection

*Lemnaceae* plants were transferred to MS medium brought to pH 4, or to a booster medium of the invention having the ingredients as detailed in the following Table 5:

TABLE 5

Agrobacterium virulence-booster medium of the invention

| Component | Amount |
|---|---|
| Caffeine (Sigma) | 150 mg |
| Fresh cell suspension from *Nicotiana tabacum* (2SH) (prepared as in Aviv and Galun, 1984) | 20 ml |
| MS basal medium (Table 1) pH brought to 4.0 with HCl prior to autoclaving | 980 ml |

Plants were microinjected under a dissecting microscope using a 1 ml sterile disposable syringe with a G-27 needle, and filled with a preparation of *Agrobacterium* suitable for transformation of *Lemnaceae*. The injections were targeted toward the meristematic zones of the plants in order to bring the bacteria into close contact with the growing meristem. In each injection, about 20 µl were injected inside the meristematic zone and each zone was injected three times.

4. Co-Cultivation

The injected *Lemna* or *Spirodela* plants were co-incubated with the suitably prepared *Agrobacterium* in MS medium (Table 1) brought to pH 4, or in the booster medium of the invention (Table 5), for 48 hours at 25° C. under cool white fluorescent bulbs (30 µE $m^{-2}s^{-1}$). Following this, the plants were washed 3 times with sterile distilled water at room temperature and cultured in MS medium (Table 1) supplemented with 400 mg/l claforan.

VII Standard X-Glue Staining Procedure

In an 1.8 ml Eppendorf tube, 5 mg of x-glue (Duchefa Biochemie BV) were dissolved in 150 µl of dimethyl formamide. Then the following staining solution was added: 10 ml of 100 mM Tris 7.0; 15 µl of 500 mM ferricyanide (stock kept frozen); 15 µl of 500 mN ferricyanide (stock kept frozen) and 100 µl of 10% Triton x-100. The plants were then transferred to a 9 cm Petri dish and 10 ml of staining solution were added. Tubes were incubated overnight at 37° C. in darkness. Then the staining solution was discarded and rinsed with distilled water. The GUS positive plants were observed with a binocular microscope.

VII. Callus Formation and Long-Term Maintenance of Morphogenetic *Spirodela*

*Spirodela punctata* plants were transferred to SP medium (Table 2) for 5 days at 26° C. under continuous fluorescent light (30 µE $m^{-2}s^{-1}$). The plants were placed under a binocular microscope, illuminated from below, and the growing daughter fronds removed, by a plucking motion using a forceps. For callus induction, mother fronds were grown on B-5 medium (Table 6, below) supplemented with 1.0% sucrose, 2 mg/l BA and 50 mg/l of Dicamba. After growing for 3 weeks on this medium, the calli were transferred to B-5 medium supplemented with 2 mg/l 2IP and 10 mg/l 2,4-D. Long-term maintenance of calli was achieved by periodical transfer every 4 weeks to fresh B-5 medium supplemented with 1.0% sucrose, 2 mg/l 2IP and 10 mg/l 2,4-D.

VIII. Rapid Regeneration f *Spirodela* Plants from Calli

*Spirodela* calli were maintained on B-5 medium (Table 6 below) supplemented with 1.0% sucrose, 3 mg/l 2IP and 10 mg/l 2,4-D. For regeneration, calli were transferred to B-5 medium supplemented with 1,0% sucrose and 2 mg/l 2IP. Fully regenerated *S. punctata* plants were efficiently obtained within 1–2 weeks. *Spirodela* calli and the regenerated plants, were grown at 26° C. under continuous fluorescent light (30 µE $m^{-2}s^{-1}$).

TABLE 6

B-5 medium (modified from Gamborg et al., 1968)

|  | Amount (mg/l) |
|---|---|
| $KNO_3$ | 2500 |
| $MgSO_4.7H_2O$ | 250 |
| $Na_2H_2PO_4.H_2O$ | 150 |
| $CaCl_2.2H_2O$ | 150 |
| $(NH_4)_2SO_4$ | 134 |
| FeEDTA | 28 |
| $H_3BO_3$ | 3 |
| $MnSO_4.H_2O$ | 10 |
| $ZnSO_4.7H_2O$ | 2 |
| $Na_2MoO_4.H_2O$ | 0.25 |
| $CuSO_4.5H_2O$ | 0.025 |
| $CoCl_2.6H_2O$ | 0.0.25 |
| KI | 0.75 |
| Nicotinic acid | 1 |
| Thiamine HCl | 10 |
| Pyridoxine HCl | 1 |
| m-inositol | 100 |
| Gelrite | 3 g/l |
| pH brought to 5.8 with NaOH prior to autoclaving | |

IX. Semi-Automated Meristem Isolation and Transformation

1. Synchronization of *Spirodela* and *Lemna* Growth By Meristem Exposure

All materials were sterilized and all procedures were carried out under aseptic conditions. Plants (10 g) were harvested in a laminar-flow sterile cabinet by pouring the contents of a culture vessel through a sterilized 10 mesh (1.7 min pore size) stainless steel sieve. The *Spirodela* or *Lemna* plants were transferred from the top of the sieve with a sterile spoon to a 1 liter-capacity sterile blender, modified to contain 6 razor blades positioned in three different planes (Blumenthal et al., 1993). The blender was filled with 250 ml of distilled, filter-sterilized water and activated for 4 sec. at 17000 rpm. The partially homogenized plants were poured aseptically from the blender through a 20 mesh (800 μ pore size) sterilized Nitex sleeve and collected on a 42 mesh (350 μ pore size) sterilized Nitex sieve. Subsequently, a jet of filter-sterilized distilled water (2 amm, 10 liters/min) was directed on top of the 20 mesh Nitex sieve in order to force all of the explant particles smaller than 800 μm to pass through, yielding a particle size population of 350–750 μm. Explant particles larger than 800 μm were transferred back to the blender with a sterile spoon, the blender activated for 3 sec at 17000 rpm, and all sieving and washing steps repeated as above. The combined size population of 350–750 μm, collected on a 42 mesh sterilized Nitex sieve, was subjected to a final sterile water-jet wash. The 350–750 μm sieved explant particles (5 g) were collected by sterile spoon and spaced in a 14 cm diameter sterile petri dish. Throughout this process, all the waste was directed by gravitational force to a 30 liter plastic container situated below the laminar flow cabinet.

2. Co-Cultivation Followed By Recovery Period

All materials were sterilized and all procedures were carried out under aseptic conditions. The sieved 350–750 μm explant particles from *Spirodela* or *Lemna*, in the 14 cm diameter petri dish, were resuspended in 15 ml of MS medium (Table 1) brought to pH 4, and then mixed with 15 ml of *Agrobacterium* previously cultured in Suppl. 2YT medium (Table 4) for 24 hrs. at 25° C. on a gyratory shaker at 250 rpm. The explant-bacteria mixture was co-cultivated for 1 hr at 25° C. and 10 μE $m^{-2}s^{-1}$. Following this, the mixture was transferred by spoon to a 100 mesh (150 μm port size) sterilized Nitex sieve. The particles excluded by the sieve were washed with 5 ml of MS medium (Table 1) brought to pH 4, and transferred to a 3 liter wide-mouth culture vessel containing 500 ml of the same medium. Co-cultivation continued for 48 hr. at 25° C. under continuous fluorescent light (30 μE $m^{-2}s^{-1}$). At the end of this period, the mixture was sieved through a 100 mesh (150 μ pore size) Nitex sieve, followed by three 200 ml rinses with distilled water. Explant particles with associated bacteria were transferred by spoon to a 3 liter wide-mouth culture vessel containing 500 ml of MS medium (Table 1) supplemented with 400 mg/l claforan and cultured for 5 days at 25° C. and 30 μE $m^{-2}s^{-1}$ light. The explants were then sieved as before, followed by separation of the floating material (most of which was living and proliferating) from the sunken, non-vital particles. This was achieved by pouring the explant material together with distilled water, into a 200 ml graduated cylinder and collecting the floating material by a straining spoon. Explants were cultured in 1 liter Erlenmeyer flasks containing 300 ml of SP medium (Table 2) for 3 days.

X. Selection and Reporter Genes

NPT II Selection and GUS staining were used to determine whether the cells of the treated plants tissue or calli were transformed, i.e. that they contained the transforming DNA. A DNA comprising the caMV 35s promoter was used followed by the *E. coli* NPT II coding sequence, which confers kanamycin resistance, as an expression vector. Stable inheritance of transgenic traits (kanamycin resistance and GUS activity) were assayed on permissive media while the NPT II gene and its products were assayed by PCR and immuno-blotting, respectively.

EXAMPLE 1

Transformation Of *Lemna* And *Spirodela* Plants By Microinjection

A color-marker reporter gene (GUS) and a gene conferring resistance to the antibiotic kanamycin (NPT II) were transferred into the *Lemnaceae* plants (*Lemna gibba* Hurfeish and *Spirodela punctata*) by *Agrobacterium tumefaciens* mediated transformation. This was achieved after suitably preparing the plants and actively promoting DNA transfer into the plant nucleus as specified above.

Booster medium of the invention (Table 5) markedly enhanced *Agrobacterium* virulence against *Lemnaceae*. Applying *Agrobacterium* to *Lemna* or *Spirodela* plants, maintained for two months in MS medium (Table 1), while omitting the booster medium drastically reduced microinjection-mediated transformation frequencies as shown in the results of the following experiments:

EXPERIMENT 1.1

49 out of 100 microinjected *Lemna* plants maintained in MS medium were GUS positive when the booster medium of the invention was used, while 3 out of 100 were GUS positive when the booster medium was omitted.

EXPERIMENT 1.2

47 out of 100 microinjected *Spirodela* plants maintained in MS medium were GUS positive when the booster medium of the invention was used, while 2 out of 100 were GUS positive when the booster medium was omitted.

Experiments 1.1 and 1.2 thus prove that the booster medium of the invention significantly raises the efficiency of transformation.

EXPERIMENT 1.3

34 out of 100 microinjected *Lemna* plants maintained in MS medium were GUS positive when the booster medium of the invention was brought to pH 4.0; 19 out of 100 were GUS positive when the booster medium was brought to pH 5.2; and 9 out of 100 were GUS positive when the booster medium was brought to pH 7.5.

EXPERIMENT 1.4

31 out of 100 microinjected *Spirodela* plants maintained in MS medium were GUS positive when the booster medium of the invention was brought to pH 4.0; 13 out of 100 were GUS positive when the booster medium was brought to pH 5.2; and 5 out of 100 were GUS positive when the booster medium was brought to pH 7.5.

These results clearly indicate that a pH below about 5.2 raises the efficiency of transformation.

The addition of caffeine, a novel agent in transformation protocols, and live tobacco cells (Aviv and Galun, 1984), was found to promote *Agrobacterium* transformation, as shown in the following experiments:

EXPERIMENT 1.5

44 out of 100 microinjected *Lemna* plants maintained in MS medium were GUS positive when co-cultivation was carried out in MS medium brought to pH 4.0, which contained caffeine and live tobacco cells; while only 33 out of 100 were GUS positive when caffeine and tobacco cells were omitted.

EXPERIMENT 1.6

39 out of 100 microinjected *Spirodela* plants maintained in MS medium were GUS positive when co-cultivation was carried out in MS medium brought to pH 4.0, which contained caffeine and live tobacco cells; while only 31 out of 100 were GUS positive when caffeine and tobacco cells were omitted.

Experiments 1.5 and 1.6 thus indicate that addition of caffeine and live tobacco cells to the booster medium of the invention raises the transformation efficiency.

EXAMPLE 2

Development Of Plants From Explant Particles

The semi-automated *Lemnaceae* blending process resulted in a purified fraction of explant particles 350–750 μm in size, from either *Lemna* or *Spirodela*, which represented approximately 50% of the total starting material. Among the 350–750 μm particles were explant particles which were seen to contain undamaged meristematic zones, from which new plants vigorously grew. Explant particles smaller than 150–350 μ gave drastically reduced number of actively growing plants. The meristem-containing explants remained green, floated and grew to maturity. All other explant particles rapidly turned yellowish-brown, eventually bleaching entirely, and most sunk to the bottom of the culture vessel. The massive death of the non-meristematic explants sections did not inhibit the normal development of new plants, which developed from the meristem-containing explant sections into mature *Lemnaceae* plants morphologically indistinguishable from non-blended plants, as demonstrated in the following experiments:

EXPERIMENT 2.1

Forty-eight hours after the blending process, 600–800 explant particles out of a total of 80,000 gave rise to tiny green *Spirodela* plants. The incipient colonies each contained 1–2 plants not longer than 1 mm. Six days after blending, these colonies consisted of 3 plants, each 2–3 mm long, and 2–3 newly developed roots (5–6 mm in length). Nine days after blending, the plants reached an average size of about 4–5 mm long and a shape both comparable to that of non-blended control *Spirodela*. At this stage, colonies contained 5–7 fronds and 5–6 fully elongated roots. These plants were further subcultured for at least 5 generations. The average biomass doubling time was 2 days and was not distinguishable from that of control plants. No somaclonal variation was observed.

EXPERIMENT 2.2

Forty-eight hours after the blending process, 300–500 explants particles out of a total of 80,000 gave rise to tiny green *Lemna* plants. The incipient colonies each contained 1 plant not longer than 1 mm. Six days after blending, these colonies consisted 2 plants, each 2–3 mm long, and 2 newly developed roots (1 mm in length). Nine days after blending, these new plants reached the average size of about 7 mm long and had a shape comparable to that of non-blended control *Lemna*. At this stage, colonies contained 4 plants and 2–4 roots. These plants were further subcultured for at least 5 generations. The average biomass doubling time was 2 days and was not distinguishable from that of control plants. No somaclonal variation was observed.

EXAMPLE 3

Analysis Of *Lemna* and *Spirodela* Plants Transformed By The Semi-Automated Meristem *Lemnaceae* Blending Process And By The Transformation Procedure A. GUS positive staining in transformed *Lemnaceae* plants following semi-automated meristem exposure and transformation.

Following transformation with *Agrobacterium* harboring the β-glucuron-idase (GUS) uidA reporter gene, explants were cultured for 3–7 days and then stained for GUS activity. The following are results of two such experiments:

EXPERIMENT 3.1

Sixteen hours after immersing *Agrobacterium*-transformed *Spirodela* colonies in a GUS reaction mixture (Jefferson, 1987), 120 of 600 colonies in one repetition, and 400 of 800 colonies in another, exhibited blue sectors, indicating that 20–50% of the explants were transformed. The size of transformed sectors ranged from 0.1 to 1 $mm^2$. Untransformed control plants did not exhibit any GUS staining. In 2 out of the 600 and 16 of the 800 colonies (0.3–2%), daughter generation plants were stained systematically blue. This indicated that the meristematic zones from which the daughter plants regenerated, had been transformed. In some colonies, the mother generation plant remained unstained while systemic GUS staining was observed in some of the daughter generation plants. This indicates that mass meristem exposure of *Spirodela* plants can lead to meristem-targeted transformation.

EXPERIMENT 3.2

Sixteen hours after immersing *Agrobacterium*-transformed *Lemna* colonies in a GUS reaction mixture (Jefferson, 1987), 60 of 300 colonies in one repetition, and 250 of 500 colonies in another, exhibited blue sectors, indicating that 20–50% of the explants were transformed. The size of transformed sectors ranged from 0.01 to 1 $mm^2$. Untransformed control plants did not exhibit any GUS staining. In 1 out of the 300 and 5 of the 500 colonies (0.3–1%), daughter generation plants were stained systemically blue. Integration of the kanamycin resistance gene In order to verify insertion and integration of the transferring DNA from *Agrobacterium*, total DNA was extracted from *Lemna* and *Spirodela* plants that were previously selected for positive GUS staining. The DNA was amplified in a PCR reaction (annealing at 55° C.) with the following primers of the NPT II coding regions:

1. 5'GCACGAGGTTCTCCGGCCGCTTGGG 3' (SEQ ID NO:1);
2. 5'GAAGGCGATGCGCTGCGAATCGGG 3' (SEQ ID NO:2).

These primers produce a 780 bp fragment within the NPT II gene. The PCR reaction product were electrophoresed on an agarose gel (0.8%) and stained with ethidium bromide. GUS-positive *Lemna* and *Spirodela* plants exhibited the expected band at the expected size for the NPTII transgene. Untransformed controls of *Lemna* or *Spirodela* plants did not contain this band. The same band at the same migration position was evident also in DNA isolated from the Ti plasmid of *Agrobacterium*, which was electrophoresised on the same gel as a positive control. These results verified that *Agrobacterium* is capable of genetically transforming *Lemna* and *Spirodela* plants.

C. Transformation of specific organs in an intact *Lemnaceae* plant

In 5% of the transformed population, expression of the introduced GUS gene was detected only in the root system. In these cases, GUS expression was detected all over the root system. This is of importance in cases where it is of interest to express the introduced gene in only a defined part of the plant such as root tissue.

EXAMPLE 4

Identification of *Agrobacterium* Strains Which Have A Specificity Towards Transformation of Meristematic Tissue in *Lemnaceae*

*Spirodela punctata* and *Lemna gibba* var. *Hurfeish* plants were maintained in SP medium (Table 2) under standard growth conditions (Procedure II). Using the standard transformation procedure (Procedure III), intact plants were co-cultivated with 5 different *A. tumefaciens* strains (EHA105 [Xiu-Qing Li et al., 1992]; EHA101 [Hood et al., 1987]; GVE3103 [Deblaere et al., 1985]; LBA4404 [Ooms et al., 1982]; and C58 [Van Larebeke et al., 1974]) each harboring Ti plasmid pME504 (shown in FIG. 1). This plasmid carries: the nptII gene, conferring resistance to the antibiotic kanamycin, under the control of the nopaline synthase promoter; the bar gene, conferring resistance to the herbicide BASTA (Thompson et al., 1987), under the control of the 35S-CaMV promoter; and the uidA gene interrupted by an intron (Vancanneyt et al., 1990), coding for the GUS reporter, also under the control of the 35S-CaMV promoter. GUS expression (Procedure VI) was determined by scoring blue spots. The tissue specificity of the different *A. tumefaciens* strains was determined by scoring the distribution of blue spots in the *Lemnaceae* plants. The data are summarized in Table 7, below.

The method involved wounding *Spirodela punctata* and *Lemna gibba Hurfeish* plants, co-cultivating the plants with $5 \times 10^8$ bacteria ml$^{-1}$, vacuum infiltration (30 mbar, 5–10 min) and further co-cultivation for 4 hr. Fronds were assayed for GUS expression 10 days after co-cultivation.

The results indicate that GUS expression in *S. punctata* co-cultivated with *A. tumefaciens* strains EHA105, EHA101 and GVE3103 was restricted mainly to daughter fronds arising from meristematic tissue, while GUS expression in *S. punctata* co-cultivated with *A. tumefaciens* strains LBS4404 and C58 was restricted mainly to wounded areas of the mother frond.

TABLE 7

| | | GUS expression (% of fronds) | | | |
| | | *Spirodela* | | *Lemna* | |
| *A. tumefac.* strain | Ti plasmid type | mother frond | daughter frond | mother frond | daughter frond |
| --- | --- | --- | --- | --- | --- |
| EHA105 | agropine | 6 | 23 | 1 | 7 |
| EHA101 | agropine | 7 | 22 | 1 | 5 |
| CVE3101 | octopine | 3 | 18 | 0 | 0 |
| LBA4404 | octopine | 10 | 3 | 0 | 0 |
| C58 | none | 8 | 1 | 0 | 0 |

EXAMPLE 5

Identification of *Agrobacterium* Strains Which Specifically Target and Transform Wounded Tissue in *Lemnaceae*

*Spirodela punctata* and *Lemna gibba Hurfeish* were maintained in SP medium (Table 2) under standard growth conditions (Procedure II). Using standard transformation procedure (Procedure III), intact plants were co-cultivated with 5 different *A. tumefaciens* strains each harboring the Ti plasmid pME504 (shown in FIG. 1). GUS expression was determined by scoring blue spots. The tissue specificity of the different *A. tumefaciens* strains was determined by the distribution of spots in the *Lemnaceae* plants. GUS expression in *S. punctata* co-cultivated with *A. tumefaciens* strains LBA4404 and C58 was restricted mainly to wounded areas of the mother frond, while GUS expression in *S. punctata* co-cultivated with *A. tumefaciens* strains EHA105, EHA101 and GVE3103 was restricted mainly to daughter fronds arising from meristematic tissue as shown in Table 7, above.

EXAMPLE 6

Use of Vacuum Infiltration For Increasing Efficiency Of Transformation Of *Lemnaceae* by *Agrobacterium*

Spirodela punctata and *Lemna gibba Hurfeish* plants were maintained in SP medium (Table 2) under standard growth condition (Procedure II). Intact plants were co-cultivated with *A. tumefaciens* strain EHA105 harboring Ti plasmid pME504 using the standard transformation procedure (Procedure III) with and without vacuum infiltration (30 mbar, 5–10 min). Transformation efficiency was determined by scoring GUS expression (blue spots). The data are shown in Table 8 below.

The method involved wounding *Spirodela punctata* var. *Helgm* and *Lemna gibba* var. *Hurfeish* plants, co-cultivating them with $5 \times 10^8$ bacteria ml$^{-1}$ (*A. tumefaciens* strain EHA105 harboring Ti plasmid pME504) and vacuum infiltration (30 mbar for 5–10 min). Control plans were wounded and co-cultured as above but without vacuum infiltration. Plants were assayed for GUS expression 10 days after co-cultivation.

The data shows an increase in transformation efficiency of 61% for *Spirodela* and 400% for *Lemna* following vacuum infiltration.

TABLE 8

| | GUS expression (% fronds) | | |
|---|---|---|---|
| | Control | Vacuum infiltrated | % increase |
| Spirodela | 18 | 29 | 61 |
| Lemna | 2 | 8 | 400 |

EXAMPLE 7

Method For Increasing Efficiency Of *Lemnaceae* Transformation By *Agrobacterium* By Exposing The Meristematic Zones Of The Mother Frond In order to partially expose the meristematic zones of *Lemnaceae* mother fronds to *Agrobacteria*, plants were placed under a binocular microscope, illuminated from below, and the growing daughter fronds removed; for example, by a plucking motion using a forceps. This procedure had no effect on the viability of the treated fronds. An experiment involving 500 *Spirodela punctata* plants, half of which had their meristematic zones exposed by daughter frond removal, resulted in an increase of GUS expression in meristematic zones from 14% (not treated) to 23% (meristematic zone exposed).

EXAMPLE 8

Method For Increasing Efficiency of *Agrobacterium* Transformation of *Lemnaceae* By Direct Dissection and Exposure of Mother Frond Meristematic Zones Following removal of the daughter fronds from the meristematic pockets of the mother frond, the mother frond was longitudinally dissected under the binocular microscope in order to fully expose its meristematic zones. An experiment was performed in which the daughter fronds were removed from 500 *Spirodela punctata* plants. Following this, 250 of these plants were also longitudinally dissected. GUS expression was monitored 10 days following co-cultivation with *A. tumefaciens* EHA105 harboring Ti plasmid pME504. GUS expression was observed in 33% of the longitudinally dissected plants, compared with 25% in the non-dissected ones.

EXAMPLE 9

Method For Increasing Stability Of *Agrobacterium* Transformation of *Lemnaceae* By Direct Dissection And Exposure Of Mother Frond Meristematic Zones The method involved treating five hundred *Spirodela punctata* as described in Example 8. For all plants, daughter fronds were first removed. In addition, one half of the mother fronds were, longitudinally dissected and co-cultivated with $5 \times 10^8$ bacteria and $ml^{-1}$ *A. tumefaciens* strain EHA105 harboring Ti plasmid pME504. Plants were vacuum infiltrated (30 mbar for 5–10 min.). Plants were assayed for GUS expression 5, 10 and 15 days after co-cultivation and their filial relationship to the dissected mother frond was recorded. The results are shown in Table 9.

TABLE 9

| | GUS expression (% fronds) | | | | | |
|---|---|---|---|---|---|---|
| | Mother frond | Daughter front generation | | | | |
| Treatment | $F_0$ | $F_1$ | $F_2$ | $F_3$ | $F_4$ | $F_5$ |
| Longitudinally dissected | 0 | 19 | 5 | 2 | 1 | 0.2 |
| Non dissected | 6 | 15 | 3 | 1 | 0 | 0.0 |

An increase in the stability of GUS expression meristematically transformed from one filial generation to the next was obtained as evident from Table 9.

EXAMPLE 10

Utilization Of *Lemnaceae* Extracts For Increasing Efficiency Of Transformation

*Spirodela punctata* plants were maintained in SP medium (Table 2) under standard growth conditions (Procedure II). Using standard transformation procedure (Procedure III), plants were co-cultivated with *A. tumefaciens* strain EHA105 harboring Ti plasmid pME504. Plants were wounded or left intact (non-wounded). Thereafter, they were co-cultivated with *A. tumefaciens* in SP medium and supplemented for various periods of time with an extract from *Spirodela* plants. Transformation efficiency was determined by scoring GUS expression (blue spots).

The method involved maintaining 500 *Spirodela punctata* plants treated as described in Procedure III. Of these 500 plants, 250 were wounded. All plants were co-cultivated with $5 \times 10^8$ bacteria $ml^{-1}$ (*A. tumefaciens* strain EHA105 harboring Ti plasmid pME504), and exposed to an extract from *Spirodela*. The extract was prepared by homogenizing 20 g of *Spirodela* plants from a one-week old culture in 50 ml phosphate buffer (pH 7.0). The homogenate was centrifuged (10 min. 10000 rpm) and the supernatant filter sterilized. The resulting *Spirodela* extract was applied for 4 hr during co-cultivation, or for this period plus the subsequent 10 days. Control plants were not exposed to the extract. All plants were assayed for GUS expression 10 days after co-cultivation.

The data summarized in Table 10 show that the presence of the *Spirodela* extract enhanced the transformation efficiency of the non-wounded plants.

TABLE 10

| Incubation with | GUS expression (% of fronds) | |
|---|---|---|
| *Spirodela* extract (h) | Wounded | Non-wounded |
| 0 | 16 | 8 |
| 4 | 17 | 10 |
| 240 | 16 | 14 |

EXAMPLE 11

Demonstration Of Transformability Of Several Species From A Number Of Genera Of *Lemnaceae*

All plants were maintained in SP medium (Table 2) under standard growth conditions (Procedure II). Using standard transformation procedure (Procedure III), plants were co-cultivated with A. tumefaciens strains EHA105 harboring Ti plasmid pME504. Table 11 summarizes the percentage of plants from different Lemnaceae species expressing GUS 10 days after co-cultivation. Gus expression in $F_1$ daughter fronds was determined for three different genera of Lemnaceae: (A) Spirodela (B); (b) Lemna; and (C) Wolffia, all inoculated with A. tumefaciens strain EHA105 (pME504).

The method involved wounding plants, co-cultivating them with $5 \times 10^8$ bacteria $ml^{-1}$ (A. tumefaciens strain EHA105 harboring Ti plasmid pME504), vacuum infiltration (30 mbar for 5–10 min) and then further co-cultivation for 30 min. Plants were assayed for GUS expression (blue stain) 10 days after co-cultivation.

The results demonstrate the general applicability of the method of the invention for Lemnaceae transformation.

TABLE 11

| Genus | Species | Strain | % stained plants |
|---|---|---|---|
| Spirodela | intermedia | 7797 | 3 |
| Spirodela | punctara | 8717 | 92 |
| Spirodela | punctara | Hegelm | 27 |
| Lemna | obscura | 7325 | 12 |
| Lemna | obscura | 7780 | 14 |
| Lemna | gibba | Hurfeish | 8 |
| Lemna | gibba | G-3 | 5 |
| Wolffia | brasiliensis | 8743 | 0.1 |
| Wolffia | australiana | 8730 | 9 |

EXAMPLE 12

Transformed Lemnaceae Expressing Antibiotic Resistance

Spirodela punctata plants obtained by standard transformation procedure (Procedure III) were placed in SP medium (Table 2) containing 2 μg/ml kanamycin. In non-transformed control cultures, newly emerging plants grew white in the presence of the antibiotic. However, following transformation and culturing in the presence of kanamycin (2 μg/ml for two months), three out of 500 (Experiment 1), and three out of 300 (Experiment 2) newly emerging plants were green and resistant to the bleaching effects of the antibiotic. This indicated that the NPTII gene was present and expressed in the green, resistant plants. The following plants were monitored: a kanamycin resistance clone 10 generations after the start of Experiment 2; a kanamycin sensitive, colony (Kn-) with bleached daughter fronds, which did not develop further in the presence of kanamycin during the two months of the experiment; a non-transformed control showing a colony with bleached daughter fronds after 7 days exposure to 2 μg/ml kanamycin. Staining of a sample taken from the kanamycin resistance clone two months after the start of Experiment 2 showed blue GUS staining in more than 80% of the fronds. The results are shown in Table 12.

The method involved wounding plants, co-cultivating them with $5 \times 10^8$ bacteria $ml^{-1}$ (A. tumefaciens strain EHA105 harboring Ti plasmid pME504) for 30 min. and vacuum infiltration (30 mbar, for 5–10 min). Transformed Spirodela punctata plants were grown in SP medium (Table 2) supplemented with 2 μg/ml kanamycin for 2 to 5 weeks. Six green plants resistant to kanamycin, and a sampling of bleached ones, were assayed for GUS expression.

The data summarized in Table 12 indicate that the green, antibiotic-resistant plants were indeed transformed.

TABLE 12

| Supplement to SP medium | GUS expression (% fronds) | |
|---|---|---|
| | Green plants | Bleached plants |
| Kanamycin (2 μg/ml) | 83 | 0 |
| BASTA (2 μg/ml) | 76 | 0 |

EXAMPLE 13

Transformed Lemnaceae Carrying Herbicide Resistance

Five hundred plants of Spirodela punctata 8717 were co-cultivated with A. tumefaciens EHA105 (pME504), carrying: the npII gene conferring resistance to the antibiotic kanamycin; the bar gene conferring resistance to the herbicide BASTA; and the uid A gene (interrupted by an intron (Vancanneyt et al., 1990) coding for the GUS reporter. Co-cultivated plants were grown in SP medium (Table 2) supplemented with 2 μg/ml BASTA for 5 weeks. The plants were periodically transferred to fresh BASTA supplemented medium every 2 weeks. Under these conditions, control plants failed to grow and eventually bleached completely after 16 days. Thirty four out of 500 plants co-cultivated with A. tumefaciens EHA105 (pME504) were resistance to the bleaching effects of the herbicide. This indicated that the bar gene was present and expressed in these green, growing plants. The following plants were monitored: green plants from a herbicide resistance clone; a BASTA sensitive, bleached plant (BASTA-) which failed to develop $F_1$ daughter fronds; and a control (non-transformed controlled showing a bleached plant. The plants were monitored 16 days after co-cultivation. Staining of a sample taken from the BASTA resistance clone 25 days after the start of the experiment showed blue GUS staining in more than 75% of the fronds. The data is summarized in Table 12. The results indicate that the green, herbicide-resistant plants, repeatedly selected on fresh BASTA supplemented medium, were indeed transformed.

EXAMPLE 14

Transformed Lemnaceae Carrying Fluorescence Reporter Genes

Spirodela punctata plants were maintained in SP medium (Table 2) under standard growth conditions (Procedure II). Using the standard transformation procedure (Procedure III), plants were co-cultivated with A. tumefaciens EHA105 (pME506) carrying the nptII gene conferring resistance to the antibiotic kanamycin; the bar gene conferring resistance to the herbicide BASTA; and the luc gene coding for the firefly luciferase reporter LUC. In parallel, other plants were co-cultivated with A. tumefaciens EHA105 (pME508) carrying the nptII gene conferring resistance to the antibiotic kanamycin; the bar gene conferring resistance to the herbicide BASTA; and a gene coding for the green fluorescence protein (GFP) of Aequorea victoria. Expression of the fluorescence reporter genes in the Spirodela plants was determined (Millar et al., 1992; Chiu et al., 1996) 10 days after co-cultivation. Expression of GFP was found throughout the frond, when viewed at a magnification of 200 times.

EXAMPLE 15

Expression Of Multiple Foreign Genes In One Transformed *Lemnaceae* Plant

*S. punctata* plants were co-cultivated with *A. tumefaciens* EHA105 (pME504), carrying: the nptII gene conferring resistance to the antibiotic kanamycin; the bar gene conferring resistance to the herbicide BASTA; and the uidA gene (interrupted by an intron (Vacanneyt et al., 1990) coding for the GUS reporter. Transformed plants were grown in SP medium (Table 2) in the presence of either 2 µg/ml kanamycin or 2 µg/ml BASTA for 2–5 weeks. Resistant green plants, as well as a sample of bleached plants, were assayed for GUS expression. The results, summarized in Table 12, demonstrate a high correlation between antibiotic- or herbicide-resistant green plants, and GUS-expressing plants. This demonstrates co-expression of multiple genes in transformed *Lemnaceae*.

EXAMPLE 16

Identification Of A High-Efficiency-Transformation Strain Of *Lemnaceae*

Experiments demonstrated a high frequency of GUS staining of a representative population of transformed *Spirodela punctata* 8717 four days after transformation. The transformation rate for this strain is >90% using the standard transformation procedure (Procedure III).

EXAMPLE 17

Stable, Non-Chimeric Transformation Of *Lemnaceae*

*Spirodela punctata* 8717 plants were maintained in SP medium (Table 2) under standard growth conditions (Procedure II). Using the standard standard transformation procedure (Procedure III), plants were co-cultivated with *A. tumefaciens* EHA105 (pME504), carrying the nptII gene conferring resistance to the antibiotic kanamycin; the bar gene conferring resistance to the herbicide BASTA; and the uidA gene interrupted by an intron (Vancanneyt et al., 1990) coding for the GUS reporter (FIG. 1). The expression of the GUS reporter gene is transformed plants was periodically determined by sampling the population at 4, 10 and 35 days after co-cultivation. Representative examples show more than 7 successive generations (attached by their stipes) of transformed plants expressing GUS throughout their tissues. This indicates stable, non-chimeric transformation of entire *Lemnaceae* plants over several generations and an extended period of time.

EXAMPLE 18

GUS Expression In *Lemnaceae* Plants Transformed With A Promoterless uidA Gene, Indicating Integration Of Foreign DNA Into the *Lemnaceae* Chromosome

*S. punctata* plants were co-cultivated with *A. tumefaciens* GV3103 (pVCGUS) (Koncz et al., 1989) which contains a promoterless GUS construct (the uidA gene interrupted by an intron). Transformed plants, expressing GUS seven days after co-cultivation, were monitored. Promoterless GUS expression is only possible if the uidA gene was integrated into the *Lemnaceae* chromosome adjacent to endogenous *Lemnaceae* regulatory sequences. As a result of random integration of the uidA gene, variability in the level of GUS expression would be expected among different transformation events. The results of the experiment show 3 different intensities of GUS blue stain, the most intense of which matches the typical strong intensity found in transformed plants under the 35S-CaMV promoter.

Table 13 summarizes the results for over 12,000 plants in 4 different experiments (each with 3 different strains of *A. tumefaciens*) which were scored for GUS staining 10 days after co-cultivation. Four thousand plants were co-cultivated with *A. tumefaciens* GV3103 lacking a binary vector (Control). None stained blue, indicating no endogenous GUS activity. Four thousand plants were co-cultivated with *A. tumefaciens* GV3103 harboring a promoterless construct (pVCGUS). Up to 1.4% of the plants stained blue, indicating a highly significant level (versus Control) of integration of the promoterless uidA gene into the *Lemnaceae* chromosome adjacent to endogenous *Lemnaceae* regulatory sequences. Four thousand plants were co-cultivated with *A. tumefaciens* GV3103 (pME504), harboring the uidA gene under the control of the 35S-CaMV promoter. Twenty eight percent of plants stained blue, indicating a relatively high level of expression using this heterologous promoter.

The method involved co-cultivation of approximately 3000 *Spirodela punctata* plants (6 gr fresh weight) in each transformation experiment (1000 plants for each of 3 constructs). Plants were scored for GUS expression 10 days after co-cultivation. The results were categorized according to the intensity of blue color: light (+), medium (++) and dark (+++).

The data in Table 13 show that the variability in intensity of GUS staining among plants co-cultivated with *A. tumefaciens* GV3103 (pVCGUS) was considerably higher than with those co-cultivated with *A. tumefaciens* GV3103 (pME504). The relatively low percentage and variability (versus Control) in intensity of GUS staining plants co-cultivated with the promoterless GUS construct are explained by random integration of this gene into the *S. punctata* chromosome and expression by various endogenous *Spirodela* promoters.

TABLE 13

| | GUS expression (No. of fronds) | | | | | | | | | | | |
|---|---|---|---|---|---|---|---|---|---|---|---|---|
| | pVC-GUS | | | | pME504 | | | | No. Ti plasmid | | | |
| | + | ++ | +++ | total | + | ++ | +++ | total | + | ++ | +++ | total |
| I | 7 | 3 | 2 | 12 | 0 | 14 | 231 | 245 | 0 | 0 | 0 | 0 |
| II | 1 | 1 | 3 | 5 | 0 | 10 | 271 | 281 | 0 | 0 | 0 | 0 |

TABLE 13-continued

| | GUS expression (No. of fronds) | | | | | | | | | | |
|---|---|---|---|---|---|---|---|---|---|---|---|
| | pVC-GUS | | | | pME504 | | | | No. Ti plasmid | | |
| | + | ++ | +++ | total | + | ++ | +++ | total | + | ++ | +++ | total |
| III | 9 | 5 | 0 | 14 | 0 | 6 | 201 | 206 | 0 | 0 | 0 | 0 |
| IV | 3 | 1 | 2 | 6 | 0 | 21 | 209 | 230 | 0 | 0 | 0 | 0 |
| Sum | | | | 37 | | | | 962 | | | | 0 |
| % (ave.) | | 0.9 | | | | 24 | | | | 0 | | |

EXAMPLE 19

Development Of An *Agrobacterium*-Mediated, In-planta, Non-Chimeric Transformation Of *Lemnaceae* Without de novo Regeneration It was demonstrated that it is possible to develop a novel transformation system in *Lemnaceae* which does not require tissue culture or in vitro regeneration procedures. The procedures enable in planta, direct meristem targeting of the transforming vehicle. In this novel system, a meristem is transformed and has the capability to continue growing and thus form the next generation. Moreover, no selection pressure is needed to avoid the growth of non-meristematic tissue within the same *Lemnaceae* plant. Examples of the validity of this approach can be seen in the results in Examples 1, 4, 6 and 10 through 18.

EXAMPLE 20

Method For Long-Term Maintenance Of Morphogenetic *Spirodela* Calli

Transient callus formation and short-term calus maintenance was previously reported in 2 species of *Lemna* (Chang and Chiu, 1978a, 1978b). Using one of these authors' callusing media (Murashige and Skoog, 1962), supplemented with 3% sucrose, 1 mg/l 2IP and 10 mg/l 2,4-D), calli were obtained from *Spirodela punctata* but callus development was arrested within 14 to 21 days. During this period, dramatic accumulation of starch (measured as an increase in iodine staining material) within the calli were observed. These calli bleached and eventually died, apparently due to starch poisoning. Long term maintenance is a prerequisite to transformation at the callus level since screening and/or selection steps are needed.

Conditions for long term maintenance of *Spirodela* calli were sought. Several different media (MS medium (Table 1), B-5 (Table 5), and concentrations of sucrose (3.0, 1.0, 0.5%) were studied in combination with a number of phytohormones (2IP; 2,4-D; Dicamba; BA, Zeatin). B-5 medium supplemented with a low concentration (1.0%) of sucrose was found to best promote long term maintenance of *Spirodela* calli under several hormonal combinations. The data in Tables 14, 15 and 16 summarize percentage callus formation and long term maintenance under several hormonal combinations. The ultimate method for callus formation and long term maintenance of morphogenetic *Spirodela* calli is given in Procedure VII. It uniquely demands a low concentration of sucrose combined with particular hormonal combinations. Using this procedure, green, growing calli were maintained for more than three months.

The method involved culturing separated *Spirodela punctata* var. *Helgm* fronds on B-5 medium supplemented with 1% sucrose and various concentrations of 2IP and 2,4-D as indicated. Callus formation was monitored after 8 weeks using a dissecting microscope. Calli were subcultured to fresh medium every 4 weeks. The results are shown in Table 14:

TABLE 14

| 2 IP (mg/l) | 2,4-D (mg/l) | Callus formation[a] No. (%) | Long term maintenance[b] No. (%) |
|---|---|---|---|
| 2 | 2 | 5 (10) | 0 (0) |
| 2 | 10 | 134 (90) | 48 (34) |
| 2 | 50 | 3 (15) | 0 (0) |
| 10 | 2 | 2 (6) | 0 (0) |
| 10 | 10 | 4 (10) | 0 (0) |
| 10 | 50 | 0 (0) | 0 (0) |

[a]Data scored after 8 weeks of culture
[b]Data scored after 12 weeks of culture In another experiment separated *Spirodela punctata* fronds were cultured on B-5 medium supplemented with 1% sucrose and various concentrations of BA and Dicamba as indicated. Callus formation was monitored after 3 weeks using a dissecting microscope. Calli were subcultured to fresh medium every 3 weeks. The results are shown in Table 15:

TABLE 15

| BA (mg/l) | Dicamba (mg/l) | Callus formation[a] No. (%) | Long term maintenance[b] No. (%) |
|---|---|---|---|
| 2 | 2 | 0 (0) | 0 (0) |
| 2 | 10 | 13 (23) | 0 (0) |
| 2 | 50 | 175 (100) | 151 (86) |
| 10 | 2 | 0 (0) | 0 (0) |
| 10 | 10 | 0 (0) | 0 (0) |
| 10 | 50 | 0 (0) | 0 (0) |

[a]Data scored after 3 weeks of culture
[b]Data scored after 6 weeks of culture

In another experiment separated *Spirodela punctata* fronds were cultured on B-5 medium supplemented with 1% sucrose and various concentrations of Zeatin and Dicamba as indicated. Callus formation was monitored after 3 weeks using a dissecting microscope. Calli were subcultured to fresh medium every 3 weeks. The results are shown in Table 16:

TABLE 16

| Zeatin (mg/l) | Dicamba (mg/l) | Callus formation[a] No. (%) | Long term maintenance[b] No. (%) |
|---|---|---|---|
| 2 | 2 | 0 (0) | 0 (0) |
| 2 | 10 | 0 (0) | 0 (0) |
| 2 | 50 | 10 (80) | 7 (70) |
| 10 | 2 | 0 (0) | 0 (0) |
| 10 | 10 | 0 (0) | 0 (0) |
| 10 | 50 | 13 (76) | 6 (46) |

[a]Data scored after 3 weeks of culture
[b]Data scored after 6 weeks of culture

EXAMPLE 21

Method For Producing Highly-Regenerative *Spirodela* Calli

The unique method for production of *Spirodela* calli is described in Procedure VII. By using this procedure in conjunction with Procedure VIII, regenerated *S. punctata* plants were efficiently obtained (Table 17 below). The combination of the two procedures represents the method for producing highly-regenerative *Spirodela* calli.

Calli of *Spirodela punctata* var. *Helgm*, maintained for 7 to 16 weeks on B-5 medium supplemented with 1% sucrose, 2 mg/l 2IP and 10 mg/l 2,4-D, were transferred to B-5 medium supplemented with 1% sucrose and different concentrations of 2IP. Regenerated plants were visually scored after 2 weeks.

TABLE 17

| 2 IP (mg/l) | Calli No. | Regenerating calli No. | (%) |
|---|---|---|---|
| 0 | 30 | 26 | 87 |
| 2 | 30 | 22 | 73 |
| 10 | 30 | 0 | 0 |

EXAMPLE 22

Method For Rapid And Highly-Efficient Regeneration Of *Lemnaceae* Plants from Calli Regeneration of frond-like structures from calli of *Lemna perpusilla* has been reported; however, the authors state that they did not observe further development of these frond-like structures even after 2 months (Chang and Hsing, 1978). In a further study, regeneration of plants from calli of *Lemna gibba* (Chang and Chiu, 1978) was reported. However, the procedure required 2 months to obtain an asexual propagating plant Chang and Chiu, 1978). Regeneration of *Spirodela* plants from calli has never been reported. Using the novel methodology of the invention for plant regeneration, intact, regenerated *S. punctata* plants were efficiently obtained within 1–2 weeks. The uniquely rapid method for *Lemnaceae* plant regeneration is given in Procedure VIII.

EXAMPLE 23

Method For Rapid And Highly-Efficient Regeneration Of True-To-Type *Spirodela* Plants From Calli Using the methodology for plant regeneration (Procedure VIII), >90% of the regenerated *S. punctata* plants visually appeared true-to-type after 3 weeks of growth in SP medium. *S. punctata* plants, viewed after 3 months of growth under standard conditions, continued to appear true-to-type. When compared with their parental progenitor with respect to growth rate, size and frond morphology no significant differences were found.

EXAMPLE 24

Method For Increasing Genetic Diversity Through Calli In Regenerating *Spirodela* Plants The ability to increase the genetic diversity in *Spirodela* is important since in several species, propagation is strictly vegetative (Landolt and Kandeler, 1987). Using the methodology for plant regeneration (Procedure VIII), several regenerated plants visually appeared aberrant and after 3 weeks of growth under standard conditions, continued to appear aberrant. When compared with their parental progenitor, significant differences were found in size (smaller), growth rate (slower) and morphology (frond shape).

EXAMPLE 25

Transformation Of *Lemnaceae* Calli By *Agrobacterium*

*Spirodela* calli were maintained on B-5 medium (Table 6) supplemented with 1.0% sucrose, 2 mg/l 2IP and 10 mg/l 2,4-D. Five hundred calli were co-cultivated with *Agrobacterium* harboring the pME504 plasmid. Following 2 days of co-cultivation, the calli were transferred to fresh medium supplemented with 30 mg/l kanamycin and 300 mg/ml carbenicillin. After 15 days, 488 calli were fully bleached. The remaining 12 green calli were transferred to fresh medium supplemented with 30 mg/l kanamycin. Three calli remained green following two additional subcultures (2 months) on fresh media containing kanamycin as above. Green calli which were maintained for more than two months on B-5 medium supplemented with 1.0% sucrose, 2 mg/l 2IP, 10 mg/l 2,4-D and 30 mg/l kanamycin were monitored. The results indicate that the persistent, green calli were resistant to kanamycin as a result of the expression of the introduced genes.

EXAMPLE 26

Production of Transgenic Calli From *Agrobacterium*-Infected Intact *Lemnaceae* Plants

*Spirodela punctata* plants were maintained in SP medium under standard growth conditions (Table 2). Using the standard transformation procedure (Procedure III), plants were co-cultivated with *A. tumefaciens* strain EHA105 harboring Ti plasmid pME504. Two days following the transformation the intact plants were cultured on B-5 medium supplemented with 10 mg/l Dicamba, 2 mg/l BA and 30 mg/l kanamycin (Procedure VII). Two green, compact calli resistant to kanamycin developed from meristematic regions after 25 days. The green growing calli were dissected from the original tissue and further subcultured on fresh medium containing 30 mg/l kanamycin for an additional 20 days. Following this transfer as well, the 2 calli remained green. The results indicate that the persistent green calli were resistant to kanamycin as a result of the introduced genes.

EXAMPLE 27

Regeneration Of Transgenic Lemnaceae Plants From Agrobacterium-Transformed Calli Spirodela punctata 8717 plants were maintained in SP medium under standard growth conditions (Table 2). Using the standard transformation procedure (Procedure III), plants were co-cultivated with A. tumefaciens strain EHA105 harboring Ti plasmid pME504. Two days following the transformation, the intact plants were cultured on B-5 medium supplemented with 10 mg/l Dicamba, 2 mg/l BA and 30 mg/l kanamycin (Procedure VII). Ten calli, resistant to kanamycin, developed from meristematic regions after 25 days. The green calli were transferred to B-5 medium supplemented with 1% sucrose, 2 mg/l 2IP and30 mg/l kanomycin. A green regenerant plant was scored after 2 weeks. This plant was transferred to the same media approximately every 2 weeks for a period of 8 months, giving rise to numerous kanamycin-resistant vegetative offsprings, hereafter designated as clone ME11. Clone ME11 has been propagated as green and kanamycin resistant in the above media for more than 65 generations.

The ability to obtain kanamycin resistant calli has been demonstrated either by production of transgenic calli from Agrobacterium-infected Lemnaceae plants (Example 25), or by production of transgenic calli from Agrobacterium-infected Lemnaceae calli (Examples 26). Since kanamycin resistant calli can be produced and true-to-type Lemnaceae plants can be efficiently and readily regenerated from calli (Procedure VIII), the technology for producing transformed Lemnaceae plants originating from antibiotic resistant calli has been demonstrated.

EXAMPLE 28

Verification Of The Long-Term Expression And Stability Of The Introduced Trait Spirodela punctata 8717 plants were maintained in SP medium under standard growth conditions (Table 2). Clone ME11, transformed as in Example 27, was propagated as green and kanamycin resistant in SP medium supplemented with 2 mg/l kanamycin for approximately 40 generations. In order to verify long-term expression and stability of the introduced traits, clone ME11 was subcultured on the same medium lacking kanamycin for approximately 60 generations. Clone ME11 was then evaluated for either kanamycin or BASTA resistance by subculturing in SP medium supplemented with either 2 mg/l kanamycin or 1.5 mg/l BASTA with or without 1% sucrose for 5–10 generations.

Control, non-transformed Spirodela punctata 8717 plants bleached and eventually died. Clone ME11 plants remained green and retained their normal growth.

These results demonstrate stable expression of kanamycin resistance in ME11 plants in spite of removal from selection pressure for more than 60 generations. They also demonstrate stable expression of BASTA resistance in spite of a lack of any selection pressure for this trait.

REFERENCES

Armitage, P, Walden, R., and Draper, J. (1992). Vectors for transformation of higher plants. In: Walden (ed), Plant Genetic Transformation and Gene Expression, Blackwell Sci. Pub., Oxford pp 1–67)

Aviv, D. and Galun E. (1984), The feeder layer technique. In Cell Culture and Somatic Cell Genetics of Plants, Vol. 1 (Academic Press, New York), pp. 199–203.

Blumenthal, A., Kahn, K., Beja, O., Galun, E., Colombini, M. and Breiman, A. (1993). Purification and characterization of the voltage-dependent anion-selective channel (VDAC) protein from wheat mitochondrial membranes. Plant Physiol., 101:579–587.

Chang W. C. and Chiu P. L. (1978) Regeneration of Lemna gibba G3 through callus culture. Z. Pflanzenphysiol. Bd 89:91–94.

Chang, W. C. and Hsing, Y. I. (1978). Callus formation and regeneration of frond-like structures in Lemna perpusilla 6746 on a defined medium. Plant Science Lett. 13:133–136.

Chiu W., Niwa, Y., Zeng, W., Hirano, T, Kobayashi, H., and Sheen, J. (1996) Engineered GFP as a vital reporter in plants. Current Biol., 6:325–330.

Christenses et al. (1996) Transgenic Res., 5: 213.

Culley, D. D. Jr., Rejmankova E, Kvet, J., and Frye J. B. (1981), Production, chemical quality and use of Lemnaceae in aquaculture, waste management and animal feeds, J. World Maricul. Soc., 12:27–49.

Deblaere, R., Bytebier, B., DeGreve, H., Deboeck, F., Schell, J., Montagu M. Van and Leemans, J. (1985). Efficient octopoine Ti-plasmid-derived vectors from Agrobacterium-mediated gene transfer to plants. Nucl. Acids Res., 13:4777–4788.

Eckes, P., Rosahl, S., Schell, J., and Willmitzer, L. (1986). Isolation and characterization of a light-inducible, organ-specific gene from potato and the analysis of its expression after tagging and transfer into tobacco and potato shoots. Mol. Gen. Genet. 199:216–224.

Hood, E. E., Fraley, R. T., Chilton, M. D. (1987). Virulence of Agrobacterium tumefacience A281 on legumes. Plant Physiol., 83:529–534.

Jefferson, R. A. (1987). Assaying chimeric genes in plants: the GUS gene fusion system. Plant Mol. Biol. Rep., 5:387–405.

Koncz, C., Martini, Mayerhofer, R., Konzk-Kalman, Z., Korber, H., Redei G. P. and Schell, J.(1989). High frequency T-DNA mediated gene tagging in plants. Proc. Natl. Acad. Sci., USA, 86:8467–8471.

Landolt, E., The family of Lemnacea—a monographic study. Vol. 1., Veroff, Geoboy. Inst. ETH, Stiftung Rubel, Zurich, pp. 274.

Landolt, E., and Kandeler, R. (1987). The family of Lemnaceae—a monographic study: Vol. 2, Veroff, Geoboy. Inst. ETH, Stiftung Rubel, Zurich, pp. 638.

Li, X., Liu, C., Ritchie, S. W., Peng, J., Gelvin, S. B. and Hodges, T. K. (1992). Factors influencing Agrobacterium-mediated transient expression of gusA in rice. Plant Mol. Biol., 20:1037–1048.

Miele, L. (1997), Plants as bioreactors for diopharmaceuticals: regulatory consideratons: Trends in biotech., 15 45–50.

Millar, A. J., Sjhort, S. R., Hiratsuka, K., Chua, N. H., and Kay, S. A. Firefly luciferase as a reporter of regulated gene expression in higher plants, Plat Mol. Biol. Rep., 10:324–337, 1992.

Murashige T. and Skoog, F, 1962. A revised medium for rapid growth and bioassays with tobacco tissue cultures. Physiol. Plant.15: 473–497.

Ngo V (1987), Boosting pond performance with aquaculture. Operations Forum 4:20–23.

Okubara, P. A., Williams, S. A., Doxsee R. A. and Tobin E. M. (1993). Analysis of genes negatively regulated by phtyochrome action in *Lemna gibba* and identification of a promoter region required for phytochrome responsiveness. *Plant Physiol.,* 101:915–924.

Ooms, G., Hooykaas, P. J. J., Ven R. J. M. van, Bleelen, P. van., Regensburg-Tuink, T. J. G., and Schilperoort, R. A. (1982). Octopine Ti-plasmid deletion of *Agrobacterium tumefacience* with emphasis on the right side of the T-region. *Plasmid,* 7:15–29.

Pen, J., Molendijk, L., Quax, W. J. Simons, P. C., Van Ooyen, A. J. J., Van den Elzen, P. J. M., Rietveld, K. and Koekema, A. (1992). Production of active *Bacillus* licheniformis a-amylase in tobacco and its application in starch liquefaction, *Bio/Technology,* 10:292–296.

Porath, D., Hepher, B. and Koton A. (1979), Duckweeds as an aquatic crops: evaluation of clones for aquaculture *Aquatic Bot.,* 7:273–278.

Posner, H. B. (1967) in Methods in Developmental Biology, Eds. Witt F. A. and Wessels N. K. (Crowell, N.Y.) pp. 301–317.

Thompson, C. J., Movva, N., Tizard, R., Crameri, R., Davies, J. E., Lauwereys and Botterman, J. (1987). Characterization of the herbicide-resistance gene bar from *Streptomyces hygroscopicus, EMBO J.,* 9:2519–2523.

Vancanneyt G., Schmidt, R., O'Connor-Sanchez, A., Willmitzer, L., and Rocha-Sosa, M. (1990), Construction of an intron-containing marker gene: Splicing of the intron in transgenic plants and its use in monitoring early events in *Agrobacterium*-mediated plant transformation. *Mol. Gen. Gent.,* 220:245–250.

VanLarebeke, N., Engler, G., Holstters, M., Van den Elscker, S., Zaenen, I., Schilperoort, R. A. and Schell, J. (1994). Large plasmid in *Agrobacterium tumefaciens* essential for crown gall-inducing ability. *Nature,* 252:169–170.

Weising et al. (1988) *Ann. Rev. Genet.,* 22: 241

The invention claimed is:

1. A method for the stable genetic transformation of *Lemnaceae* whole plants, plant tissue or callus, which comprises:
   brining the *Lemnaceae* whole plant, plant tissue or callus into contact with *Agrobacterium* cells containing a transforming DNA molecule; and
   incubating the *Lemnaceae* whole plant, plant tissue or callus with the *Agrobacterium* cells, whereby cells in said whole plant, plant tissue or callus become stably transformed with said DNA,
   wherein the *Agrobacterium* cells are brought into contact, prior to or during the transformation method, with a booster medium that enhances the *Agrobacterium* cells' virulence, said booster medium comprising a fresh cell suspension of dicotyledonous plants or comprising *Lemnaceae* plant extracts, and further comprising caffeine at a concentration of 100–500 mg per liter of medium.

2. A method according to claim 1, wherein the *Lemnaceae* whole plant, plant tissue or callus is of the genus *Spirodela, Lemna* or *Wolffia.*

3. A method according to claim 1, wherein the *Agrobacterium* cells specifically target the plant's meristematic tissue.

4. A method according to claim 3, wherein the *Agrobacterium* cells are *A. tumefaciens* strains EHA105, EHA101 or GVE3103.

5. A method according to claim 1, wherein the *Agrobacterium* cells target wounded regions in the plant.

6. A method according to claim 5, wherein the *Agrobacterium* is *A. tumefaciens* strains LBA4404 or C58.

7. A method according to claim 1, wherein, during the incubation of the *Lemnaceae* plant tissue with the *Agrobacterium* cells, vacuum infiltration is applied.

8. A method according to claim 1, wherein, prior to incubation of the *Lemnaceae* plant tissue with the *Agrobacterium* cells, the plant's meristematic zone is exposed by removal of the daughter fronds.

9. A method for the genetic transformation of a *Lemnaceae* plant, comprising:

SEQUENCE LISTING

<160> NUMBER OF SEQ ID NOS: 2

<210> SEQ ID NO 1
<211> LENGTH: 25
<212> TYPE: DNA
<213> ORGANISM: Agrobacterium

<400> SEQUENCE: 1
gcacgaggtt ctccggccgc ttggg                                                25

<210> SEQ ID NO 2
<211> LENGTH: 24
<212> TYPE: DNA
<213> ORGANISM: Agrobacterium

<400> SEQUENCE: 2
gaaggcgatg cgctgcgaat cggg                                                 24 cutting the plant into particles of a size such that they still contain undamaged meristematic tissue capable of developing into full plants;

incubating said particles with *Agrobacterium* cells containing transforming DNA molecules, whereby said transforming DNA is introduced into meristematic cells in said particles; and producing transformed plants from the transformed meristematic tissue.

10. A method according to claim 9, wherein the particles have diameters, the average of which is above 150 µm.

11. A method according to claim 10, wherein the particles have diameters, the average of which is about 150 µm to about 750 µm.

12. A method according to claim 1, wherein the transformation process takes place in a media having a pH below about 5.2.

13. A method according to claim 1, wherein the booster medium comprises a fresh cell suspension obtained from a dicotyledonous plant.

14. A method according to claim 13, wherein the fresh cell suspension is at a concentration of 1–10% (w/v).

15. A method according to claim 13, wherein the fresh cell suspension of a dicotyledonous plant is obtained from the family of *Solanaceae*.

16. A method according to claim 1, wherein the booster medium is a plant culture medium having a pH of about 3.5 to 4.2, and comprising 1–10% (w/v) of fresh cell suspension of *Nicotiana tabacum* and 100–500 mg per liter of caffeine.

17. A method for the stable genetic transformation of *Lemnaceae* whole plants, plant tissue or callus, which comprises:

brining the *Lemnaceae* whole plant, plant tissue or callus into contact with *Agrobacterium* cells containing a transforming DNA molecule; and incubating the *Lemnaceae* whole plant, plant tissue or callus with the *Agrobacterium* cells, whereby cells in said whole plant, plant tissue or callus become stably transformed with said DNA, wherein the *Agrobacterium* cells are brought into contact, prior to or during the transformation method, with a booster medium that enhances the *Agrobacterium* cells' virulence, said booster medium being a *Lemnaceae* plant extract.

18. A method according to claim 17, where the *Lemnaceae* plant extract is a *Spirodela punctata* extract.

19. A method according to claim 17, wherein the *Lemnaceae* whole plant, plant tissue or callus is of the genus *Spirodela*, *Lemna* or *Wolffia*.

20. A method according to claim 17, wherein the *Agrobacterium* cells specifically target the plant's meristematic tissue.

21. A method according to claim 20, wherein the *Agrobacterium* cells are *A. tumefaciens* strains EHA105, EHA101 or GVE3103.

22. A method according to claim 17, wherein the *Agrobacterium* cells target wounded regions in the plant.

23. A method according to claim 22, wherein the *Agrobacterium* is a *A. tumefaciens* strains LBA4404 or C58.

24. A method according to claim 17, wherein, during the incubation of the *Lemnaceae* plant tissue with the *Agrobacterium* cells, vacuum infiltration is applied.

25. A method according to claim 17, wherein, prior to incubation of the *Lemnaceae* plant tissue with the *Agrobacterium* cells, the plant's meristematic zone is exposed by removal of the daughter fronds.

26. A method according to claim 17, wherein the transformation process takes place in a media having a pH below about 5.2.

* * * * *